US009034387B2

(12) United States Patent
Kundu et al.

(10) Patent No.: US 9,034,387 B2
(45) Date of Patent: May 19, 2015

(54) INTRINSICALLY FLUORESCENT CARBON NANOSPHERES AND A PROCESS THEREOF

(75) Inventors: Tapas Kumar Kundu, Karnataka (IN); Eswaramoorthy Muthusamy, Sr., Karnataka (IN); Ruthrotha Selvi Bharatha Vikru, Karnataka (IN); Dinesh Jagadeesan, Karnataka (IN)

(73) Assignee: Jawaharlal Nehru Centre for Advanced Scientific Research, Karnataka (IN)

( * ) Notice: Subject to any disclaimer, the term of this patent is extended or adjusted under 35 U.S.C. 154(b) by 814 days.

(21) Appl. No.: 12/681,596

(22) PCT Filed: Sep. 30, 2008

(86) PCT No.: PCT/IN2008/000632

§ 371 (c)(1),
(2), (4) Date: Apr. 2, 2010

(87) PCT Pub. No.: WO2009/044410

PCT Pub. Date: Apr. 9, 2009

(65) Prior Publication Data

US 2010/0215760 A1 Aug. 26, 2010

(30) Foreign Application Priority Data

Oct. 3, 2007 (IN) ............................ 2218/CHE/2007

(51) Int. Cl.
| | |
|---|---|
| *A61K 9/51* | (2006.01) |
| *A61K 47/36* | (2006.01) |
| *A61K 9/14* | (2006.01) |
| *C12N 5/02* | (2006.01) |
| *C07C 235/64* | (2006.01) |
| *A61K 31/235* | (2006.01) |
| *A61K 47/00* | (2006.01) |
| *A61P 3/10* | (2006.01) |
| *A61P 11/06* | (2006.01) |
| *A61P 35/00* | (2006.01) |
| *A61P 31/18* | (2006.01) |

(52) U.S. Cl.
CPC ............ *A61K 9/5115* (2013.01); *C07C 235/64* (2013.01); *A61K 31/235* (2013.01); *A61K 47/00* (2013.01); *A61K 9/5192* (2013.01); *A61K 9/5176* (2013.01)

(58) Field of Classification Search
CPC ........................... A61K 31/235; A61K 9/5176
See application file for complete search history.

(56) References Cited

U.S. PATENT DOCUMENTS 7,332,629 B2 * 2/2008 Kundu et al. ................. 564/176
2006/0167107 A1 * 7/2006 Kundu et al. ................. 514/617

FOREIGN PATENT DOCUMENTS

EP  1 760 467 A1  3/2007
WO  WO 2006/010083 A  1/2006

OTHER PUBLICATIONS

Mantelingu et al., Journal of Physical Chemistry B, 111: 4527-4534 (2007).*
Hicks, Surface Enhanced Raman Spectroscopy, Michigan State University CEM 924 (2001) accessed at http://www.cem.msu.edu/~cem924sg/ChristineHicks.pdf Aug. 29, 2012.*
Brigger et al., Advanced Drug Delivery Reviews, 54: 631-651 (2002).*
Selvi et al., Nano Letters, 8(10): 3182-3188 (2008) (supporting information accessed at http://pubs.acs.org/doi/suppl/10.1021/nl801503m, on Aug. 30, 2012).*
Balasubramanyam et al., Journal of Biological Chemistry, 279(32): 33716-33725 (2004).*
Xu et al., Chemical Engineering Science, 61: 1027-1040 (2006).*
Balasubramanyam, K. et al., "Small Molecule Modulators of Histone Acetyltransferase p300," *Journal of Biological Chemistry*, May 23, 2003, pp. 19134-19140, vol. 278, No. 21.
Barbé, C. et al., "Silica Particles: A Novel Drug-Delivery System," *Advanced Materials*, Nov. 2004, pp. 1959-1966, vol. 16, Issue 21.
Berger, S.L., "The Complex Language of Chromatin Regulation During Transcription," *Nature*, May 24, 2007, pp. 407-412, vol. 447.
Choy, J. H., "Inorganic Layered Double Hydroxides as Nonviral Vectors," *Angewandte Chemie International Edition*, 2000, p. 4042-4045, vol. 39.
Dinesh, J., "Use of Amorphous Carbon Nanotube Brushes as Templates to Fabricate GaN Nanotube Brushes and Related Materials," *Journal of Physical Chemistry C*, 2007, pp. 510-513, vol. 111, No. 2.
Fenic, I., et al., "In Vivo Application of Histone Deacetylase Inhibitor Trichostatin-A Impairs Murine Male Meiosis," *Journal of Andrology*, Mar./Apr. 2008, p. 172-185, vol. 29, No. 2.
Holowka, E. et al, "Polyarginine Segments in Block Copolypeptides Drive Both Vesicular Assembly and Intracellular Delivery," *Nature Materials*, 2007, pp. 52-57, vol. 6.

(Continued)

*Primary Examiner* — Kortney L Klinkel
*Assistant Examiner* — Lisbeth C Robinson
(74) *Attorney, Agent, or Firm* — Fenwick & West LLP (57) ABSTRACT

The present invention provides solution to the problem involved in delivery of active molecules to nucleus. More particularly, the invention provides intrinsically fluorescent and inherently surface functionalized carbon nanospheres which are non-toxic. Also, these carbon nanospheres [CSP] were adsorbed with CTPB [CSP-CTPB] and the adsorbed CSP-CTPB are permeable to cells with nuclear targeting ability. In addition, the present invention provides a composition, a process to prepare the composition comprising CSP with adsorbed active/therapeutic molecules. Further, the instant invention provides a method for delivering active molecules inside a cell nucleus.

9 Claims, 11 Drawing Sheets

(56) References Cited

OTHER PUBLICATIONS

Kam, N. et al, "Nanotube Molecular Transporters: Internalization of Carbon Nanotube-Protein Conjugates into Mammalian Cells," *Journal of American Chemistry Society*, 2004, pp. 6850-6851, vol. 126.

Lacerda, L. et al., "Carbon Nanotube Cell Translocation and Delivery of Nucleic Acids in Vitro and in Vivo," *Journal of Materials Chemistry*, 2008, pp. 17-22, vol. 18.

Lacerda, L. et al., "Intracellular Trafficking of Carbon Nanotubes by Confocal Laser Scanning Microscopy," *Advanced Materials*, 2007, pp. 1480-1484, vol. 19.

Li, B. et al. "The Role of Chromatin During Transcription," *Cell*, Feb. 23, 2007, p. 707-719, vol. 128, No. 4.

Liu, H. et al., "Fluorescent Carbon Nanoparticles Derived from Candle Soot," *Angewandte Chemie International Edition*, 2007, pp. 6473-6475, vol. 46, Issue 34.

Liu, Z. et al., "In Vivo Biodistribution and Highly Efficient Tumour Targeting of Carbon Nanotubes in Mice," *Nature Nanotechnology*, 2007, pp. 47-52, vol. 2.

Liu, Z. et al., "siRNA Delivery into Human T Cells and Primary Cells with Carbon-Nanotube Transporters," *Angewandte Chemie International Edition*, 2007, pp. 2023-2027, vol. 46.

Mai, A. "The Therapeutic Uses of Chromatin-modifying Agents," *Expert Opinion on Therapeutic Targets*, Jun. 2007, pp. 835-851, vol. 11, No. 6.

Mantelingu, K. et al., "Specific Inhibition of p300-HAT Alters Global Gene Expression and Represses HIV Replication," *Chemistry & Biology*, 2007, pp. 645-657, vol. 14.

Michalet, X. et al. "Quantum Dots for Live Cells, in Vivo Imaging, and Diagnostics," *Science*, Jan. 2005, pp. 538-544, vol. 307, No. 5709.

Nasongkla, N. et al. "Multifunctional Polymeric Micelles as Cancer-Targeted, MRI-Ultrasensitive Drug Delivery Systems," *Nano Letters*, 2006, pp. 2427-2430, vol. 6, No. 11.

PCT International Search Report and Written Opinion, PCT/IN2008/000632, Feb. 19, 2009, 9 Pages.

Roth, S.Y. et al., "Histone Acetyltransferases," *Annual Review of Biochemistry*, 2001, pp. 81-120, vol. 70.

Schroeder, U. et al., "Efficacy of Oral Dalargin-loaded Nanoparticle Delivery across the Blood-Brain Barrier," *Peptides*, 1998, pp. 777-780, vol. 19, No. 4.

Schroeder, U. et al., "Nanoparticles, a Drug Carrier System to Pass the Blood-brain Barrier, Permit Central Analgesic Effects of I.V. Dalargin Injections," *Brain Research*, Feb. 26, 1996, pp. 121-124, vol. 710.

Schroeder, U. et al., "Nanoparticle Technology for Delivery of Drugs across the Blood-brain Barrier," *Journal of Pharmacological Sciences*, Nov. 1998, pp. 1305-1307, vol. 87, No. 11.

Srinivas, P. et al., "Plumbagin Induces Reactive Oxygen Species, Which Mediate Apoptosis in Human Cervical Cancer Cells," *Molecular Carcinogenesis*, Aug. 2004, pp. 201-211, vol. 40, Issue 4.

Sun, X., et al., "Colloidal Carbon Spheres and Their Core/Shell Structures with Noble-Metal Nanoparticles," *Angewandte Chemie International Edition*, 2004, pp. 597-601, vol. 43.

Swaminathan, V. et al., "Small Molecule Modulators in Epigenetics: Implication in Gene Expression and Therapeutics," *Chromatin and Disease: Subcellular Biochemistry*, 2007, pp. 399-428, vol. 41.

Thompson, P. et al., "Regulation of the p300 HAT Domain Via a Novel Activation Loop," *Nature Structural & Molecular Biology*, Apr. 2004, pp. 308-315, vol. 11, No. 4.

Worle-Knirsch, J.M. et al., "Oops They Did It Again! Carbon Nanotubes Hoax Scientists in Viability Assays," *Nano Letters*, 2006, pp. 1261-1268, vol. 6, No. 6.

Xu, P.; et al., "Targeted Charge-Reversal Nanoparticles for Nuclear Drug Delivery," Angewandte Chemi. Int. Ed., 2007, pp. 4999-5002, vol. 46.

Zhu, H. et al., "Loading of Hydrophobic Materials into Polymer Particles: Implications for Fluorescent Nanosensors and Drug Delivery," *Journal of American Chemistry Society*, 2005, pp. 13448-13449, vol. 127, No. 39.

\* cited by examiner

INTRINSICALLY FLUORESCENT CARBON NANOSPHERES AND A PROCESS THEREOF

FIELD OF THE INVENTION

The present invention is in relation to the filed of Nanotechnology, More particularly, the present invention relates to the field of nanomaterials being used as delivery vehicles for introducing molecules into the cells, especially small molecule modulators of histone modifying enzymes. This has potential therapeutic uses in various diseases for targeted drug delivery.

BACKGROUND AND PRIOR ART OF THE INVENTION

Diseases like cancer, AIDS, diabetes, asthma are the major causes of concern in developing countries like India. With the recent advances in nanoscience, it has been possible to employ nanoparticles to deliver the necessary drugs inside specific cancerous cells. A number of factors like permeability of the particles inside the cells, cytotoxicity, biodegradability, surface functional groups, fluorescence, economically viable synthetic methods must be considered for developing the nanoparticles for intracellular drug delivery applications. Most often the nanoparticles require several chemical modifications to load the concerned molecules on their surfaces. Furthermore, tracking the nanoparticles during the intracellular trafficking can be made possible only when they are fluorescently tagged. There is every likelihood that these modifications can change the biological fate of the nanoparticles. Though the transport of nucleic acids, proteins, peptides and drug molecules across the cell membrane using these nanoparticles/nanotubes have been demonstrated, their inefficiency to breach the nuclear membrane limits their use in many applications where the drug molecules should be delivered inside the nucleus. Treatment of diseases based on the reversiblel modifications of histones by HATs (histone acetyltransferase) and HDACs (histone deacetylases) whose dysfunction cause many diseases have become the new generation therapeutic targets. Therefore, it is highly important to develop new nanomaterials that can specifically enter the cancerous nuclei and deliver the molecules which can in turn influence (activate or inhibit) the chromatin modifiying enzymes.

OBJECTIVES OF THE PRESENT INVENTION

The principle objective of the present invention is to prepare intrinsically fluorescent carbon nanospheres so as to achieve targeted drug delivery.

Another objective of the present invention is to develop a process for the preparation of intrinsically fluorescent carbon nanospheres.

Yet another object of the present invention is to achieve intracellular delivery of active drug moieties followed by entry into the nucleus.

Still another object of the present invention is to achieve intranuclear delivery of p300 histone acetyltransferase activator CTPB and other modulators of chromatin modifying enzymes.

Still another, object of the present invention is to achieve carbon nanospheres which are intrinsically fluorescent and inherently surface functionalized.

STATEMENT OF THE INVENTION

Accordingly, the present invention provides an intrinsically fluorescent carbon nanosphere; a process for preparation of intrinsically fluorescent carbon nanosphere, said process comprising step of polymerization of sugar solution to obtain the intrinsically fluorescent carbon nanospheres; a composition comprising intrinsically fluorescent carbon nanospheres and active molecule(s), optionally along with acceptable excipients; a process for preparation of a composition comprising intrinsically fluorescent carbon nanospheres and active molecule(s), said process comprising step of adsorbing the active molecule(s) over the carbon nanospheres to obtain the composition; and a method of delivering active molecules inside a cell nucleus, said method comprising step of administering pre-determined amount of composition comprising intrinsically fluorescent carbon nanosphere and the active molecules, optionally along with acceptable additives.

DETAILED DESCRIPTION OF THE PRESENT INVENTION

The present invention is in relation to intrinsically fluorescent carbon nanosphere.

In another embodiment of the present invention, the carbon nanosphere has particle size ranging from about 100 nm to about 500 nm, preferably about 400 nm.

In yet another embodiment of the present invention, said carbon nanosphere is dispersible in solvent selected from a group comprising water, toluene, chloroform, ethanol and methanol.

In still another embodiment of the present invention, said carbon nanosphere is inherently surface functionalized.

In still another embodiment of the present invention, said carbon nanosphere is non toxic.

In still another embodiment of the present invention, said carbon nanosphere is derived from sugar, preferably glucose.

The present invention is in relation to a process for preparation of intrinsically fluorescent carbon nanosphere, said process comprising step of polymerization of sugar solution to obtain the intrinsically fluorescent carbon nanospheres.

In another embodiment of the present invention, said polymerization of sugar solutions is performed by hydrothermal reaction at a temperature of about 180° C.

In yet another embodiment of the present invention, said sugar is selected from a group comprising glucose, sucrose, fructose, cyclodextrin, maltose, starch and cellulose.

In still another embodiment of the present invention, said carbon nanosphere is inherently surface functionalized with acidic, ketone, $\alpha$, $\beta$ unsaturated aldehydes and alcoholic functional groups.

The present invention is in relation to a composition comprising intrinsically fluorescent carbon nanospheres and active molecule(s), optionally along with acceptable excipients.

In another embodiment of the present invention, said composition is permeable to cell with nucleus targeting ability.

In yet another embodiment of the present invention, said active molecule(s) is selected from a group comprising p300 histone acetyltransferase activators, 4-chloro-3-trifluoromethylphenyl-2-ethoxybenzamide, DNA, polycations, peptides, antibodies and RNA.

In still another embodiment of the present invention, said composition preferably comprises intrinsically fluorescent carbon nanospheres adsorbed with 4-chloro-3-trifluoromethylphenyl-2-ethoxybenzamide for activation of histone acetyltransferase p300.

In still another embodiment of the present invention, said composition preferably comprising intrinsically fluorescent carbon nanospheres at a concentration of about 2 mg/mL adsorbed with 4-chloro-3-trifluoromethylphenyl-2-ethoxybenzamide at a concentration of about 3 mg/mL.

In still another embodiment of the present invention, the excipients are selected from a group comprising granulating agents, binding agents, lubricating agents, disintegrating agents, sweetening agents, coloring agents, flavoring agents, coating agents, plasticizers, preservatives, suspending agents, emulsifying agents and spheronization agents or any combinations thereof.

The present invention is in relation to a process for preparation of a composition comprising intrinsically fluorescent carbon nanospheres and active molecule(s), said process comprising step of adsorbing the active molecule(s) over the carbon nanospheres to obtain the composition.

In another embodiment of the present invention, the adsorption is followed by centrifugation for time period ranging from about 7 min to about 10 min followed by washing, drying and sonicating to obtain the carbon nanospheres with the adsorbed active molecule(s).

In yet another embodiment of the present invention, said active molecules are selected from a group comprising p300 HAT activators, 4-chloro-3-trifluoromethylphenyl-2-ethoxybenzamide, DNA, polycations, peptides, antibodies and RNA.

In still another embodiment of the present invention, said composition preferably comprising intrinsically fluorescent carbon nanospheres at a concentration of about 2 mg/mL adsorbed with 4-chloro-3-trifluoromethylphenyl-2-ethoxybenzamide at a concentration of about 3 mg/mL.

The present invention is in relation to a method of delivering active molecules inside a cell nucleus, said method comprising step of administering pre-determined amount of composition comprising intrinsically fluorescent carbon nanosphere and the active molecules, optionally along with acceptable additives.

In yet another embodiment of the present invention, said carbon nanosphere with adsorbed active molecules are permeable to cell with nucleus targeting ability.

In still another embodiment of the present invention, said active molecules are selected from a group comprising p300 HAT activators, (4-chloro-3-trifluoromethylphenyl)-2-ethoxybenzamide), DNA, polycations, peptides, antibodies and RNA.

In still another embodiment of the present invention, said composition is non toxic.

In still another embodiment of the present invention, said composition preferably comprising intrinsically fluorescent carbon nanospheres adsorbed with 4-chloro-3-trifluoromethylphenyl-2-ethoxybenzamide for activation of histone acetyltransferase p300.

In still another embodiment of the present invention, said composition induces hyperacetylation of histone acetyltransferase in its proximal chromatin domain, increases RNA polymerase II, p300 autoacetylation and in vivo hyperacetylation and transcriptional activation.

In still another embodiment of the present invention, said composition crosses blood brain barrier and gets localized in brain and also in spleen and liver.

In still another embodiment of the present invention, said composition activates p300 histone acetyltransferase activity followed by transcription in brain.

Use of nanomaterials in biology has opened doors to a better understanding of cellular processes through imaging and thereby improved therapeutic procedures especially in drug delivery.[3] Nanoparticles such as silica,[4] LDH clay,[5] micelles,[6] polymer nanoparticles[7] and carbon nanotubes[8,9] are being actively explored for the intracellular drug delivery purpose. Most often these nanoparticles require several surface chemical modifications to attach the drug molecules and additional fluorescent tags[10, 11] that inevitably affects the cellular uptake and metabolism of the nanomaterial. Despite their use in transporting nucleic acids, proteins, and drug molecules across the cell membrane, the inefficiency to breach the nuclear membrane limits their use in many applications. On the other hand nuclear targeting carriers like peptides and polyethyleneimines face intense serum inhibition due to their highly positive charged surfaces.[12] Here we report, the carbon nanospheres (CSP)[1] derived from hydrothermal treatment of glucose overcome all the above shortcomings and enter the cell nuclei. Remarkably, these CSP are intrinsically fluorescent and do not require any additional fluorescent tags to track them inside the cells. Furthermore, the CSP are readily dispersible in water without any prior surface modifications and could successfully deliver a therapeutically potential, cell impermeable molecule, CTPB[2] inside the nucleus.

The Applicant hereby reports the following in the current invention:

1. Amorphous Carbon nanospheres which are inherently fluorescent.
2. These carbon spheres can be prepared by the hydrothermal decomposition of glucose at 180° C. and can also be synthesized in the form of nanotubes by confining the reaction with in a porous membrane.
3. The carbon spheres (100-500 nm) thus obtained are made up of dense hydrophobic core of polyaromatic units covered by layers of highly functionalized carbon chains of few nm thickness (functionalized with polymeric alcohols, salicylaldehyde groups and $\alpha,\beta$ unsaturated aldehydes) with negatively charged surface.
4. They are easily dispersed in water and many organic solvents like ethanol, toluene etc. The existence of both hydrophobic core and hydrophilic surface on the carbon spheres helps them to disperse easily in polar and non-polar solvents.
5. Photoluminescence studies on carbon spheres show a weak emission at 660 nm on excitation at 514 nm, attributed to the radiative relaxation of excited electrons (possibly due to the presence of conjugated aromatic systems). This helps to image the carbon spheres in the confocal microscope without the aid of any fluorescent tag over extended periods, which is an added advantage over the risks involved in the case of quantum dots or organic dyes.
6. The presence of optimum hydrophilicity and hydrophobicity enhances the cell internalization of carbon spheres. The entry of the carbon spheres inside the cells takes about 1 h and at 3 h they reach the perinuclear region followed by their entry into the nucleus.
7. These carbon spheres were used to deliver the only known p300 histone acetyltransferase activator CTPB into the cells and thereby induce hyperacetylation and transcriptional activation.

Further modifications of the nanospheres are underway so as to introduce specific targeting of the molecules. Therefore, this inherently fluorescent, easily permeable to the cell nuclei, carbon nanospheres will be highly useful as potential drug delivery vehicles.

Figure 1:
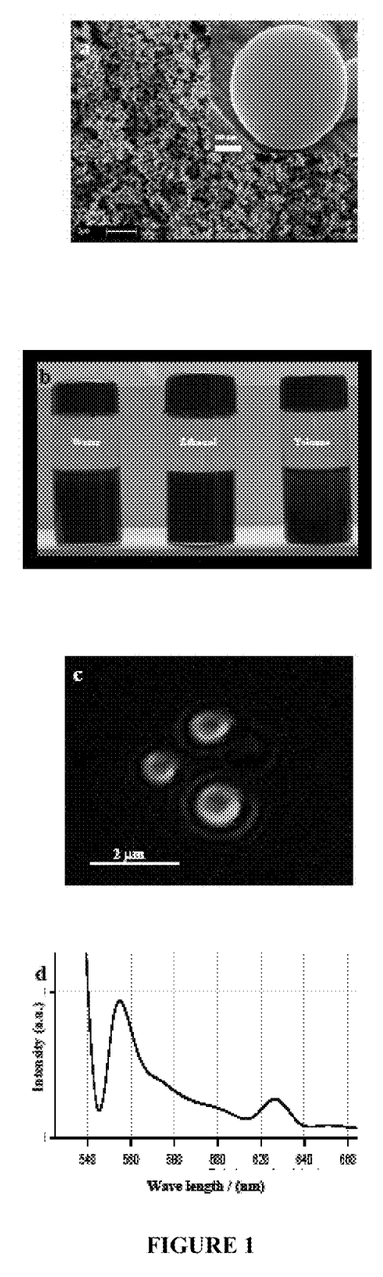
FIG. 1
(a) Scanning electron microscopy image of glucose derived carbon nanospheres (CSP)
(b) Carbon nanospheres dispersed in Water, Ethanol and Toluene
(c) Confocal Laser scanning image of carbon nanosphere
(d) Emission spectrum obtain in situ in the confocal microscope FIG. 2
(a) Time course study of entry of carbon nanospheres in HeLa cells after 30 min, 1 h, 3 h and 24 h.
(b) Histogram showing MTS based cytotoxic assay for carbon nanospheres (blue bars) and plumbagin (red bars)
(c) Graph showing zeta potential of carbon nanospheres
(d) Graph showing zeta potential of carbon nanospheres at different pH observed over a period of 56 h.
(e) Graph showing zeta potential of carbon nanospheres in water (red) and carbon nanospheres soaked in serum containing cell medium (blue)
(f) Graph showing zeta potential of carbon nanosphere (black) and carbon nanosphere adsorbed with polycation (red).
(g) Graph showing zeta potential of carbon nanosphere (black) and carbon nanosphere adsorbed with DNA after $1^{st}$ wash (red), after $2^{nd}$ wash (green) and after $3^{rd}$ wash (blue).
(h) EDX analysis of carbon spheres adsorbed with DNA after three cycles of washing with water FIG. 3
(a) X-ray crystal structure of CTPB showing ball and stick model
(b) SEM image panels of carbon nanospheres absorption with CTPB
(c) & (d) Top panel showing confocal image of HeLa cells, bottom panel showing intensity profile of the image arising from Hoechst staining FIG. 4
(a) Immunoblot analysis of histones isolated from HeLa cells
(b) & (c) Immunofluorescence analysis of carbon nanospheres alone and CTPB-carbon nanospheres probed for fluorescent tagged antibody against acetylated p300 HAT
(d) Immunofluorescence images of HeLa cells treated CSP, CTPB-CSP
(e) Intensity profile of cells treated with CSP and CTPB-CSP
(f) Induction in ATF6 gene expression on CTPB mediated hyperacetylation (lane 2) and CSP alone treated cells (lane 1)

FIG. 1. Intrinsically fluorescent carbon nanosphere. (a) Scanning Electron Microscopy Image of the glucose derived carbon spheres. Inset shows an isolated carbon sphere measuring about 400 nm. (b) Carbon spheres were dispersed (2 mg/mL) in solvents of different polarity like water, ethanol and toluene. The digital image was obtained after allowing the suspensions to stand for 1 h. The surface of the sphere was amphiphilic as evident from the stability of the dispersions. (c) Confocal Laser scanning image of the carbon sphere obtained by placing a drop of water suspension containing carbon spheres. The fluorescence is obtained by exciting the spheres at 514 nm. (d) Emission spectrum obtained in situ in the confocal microscope. The broad peak of emission occurs from 540-560 nm with a maximum at 550 nm.

Figure 2:
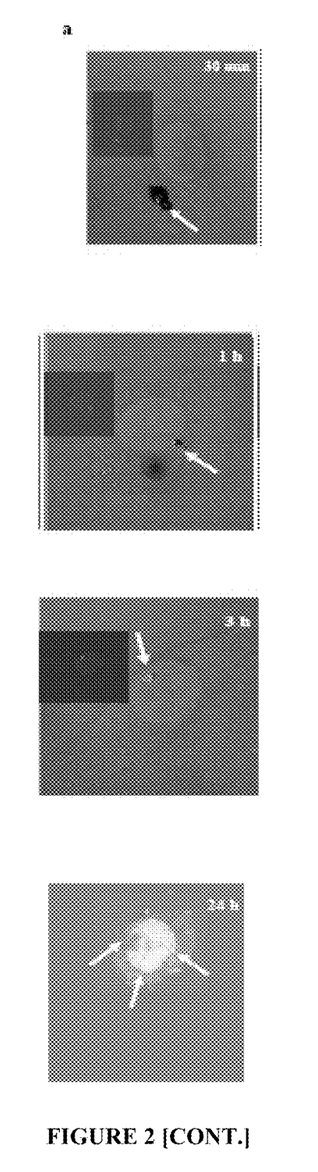

FIG. 2. CSP is nontoxic to HeLa cells. (a) Time course study of entry of CSP in HeLa cells after 30 min, 1 h, 3 h and 24 h. White arrows indicate the CSP. Inset is the image without phase contrast. (b) MTS based cytotoxicity assay, blue bars represent CSP treated cells, red bar represents plumbagin treated cells. Control untreated cells (lane I), CSP or plumbagin treated cells (lane II—10 μg/ml; lane III—20 μg/ml; lane IV—50 μg/ml; lane V—100 μg/ml; lane VI—200 μg/ml). (c) Zeta potential of CSP dispersed in water at different pH values A) 8, B) 7.3, C) 6, D) 5, E) 4. The zeta potential was measured after an equilibration time of 2 h. (d) Zeta potential of the carbon sphere at different pH was observed over a period of 56 h. (e) Zeta potential of carbon spheres in water at pH 7.3 (red), carbon spheres soaked in the serum containing cell medium at pH 7.3 (blue). (f) Zeta potential of carbon sphere dispersed in water at pH 7.3 is at −24 mV. The spheres soaked in a 20% aqueous solution of polydiallyldimethylammonium chloride for 20 minutes show a good adsorption as indicated by the shift in the surface potential to +40 mV. This also suggests the possibility of loading cationic polypeptides onto the surface of carbon sphere by simple adsorption. (g) Adsorption of negatively charged molecule like DNA was studied on the surface of the carbon spheres. The adsorption of DNA was carried out by soaking 250 μg dispersed in 10 ml of deionised water containing 5 mg of DNA pH 7.3 showing signs of adsorption of DNA on carbon spheres. But, increased number of washing in water restores the zeta potential back to −24 mV suggesting weak adsorption. (h) EDX analysis of carbon spheres adsorbed with DNA after three cycles of washing with water FIG. 3. Small molecule HAT activator binds to the CSP and induces hyperacetylation within HeLa cells. (a) X-ray crystal structure of CTPB showing the ball and stick model view of the compound. The color coding of the atoms is as follows: light blue, carbon; white, hydrogen; red, oxygen; grey, fluorine; green, chlorine; dark blue, nitrogen. (b) SEM image of the carbon spheres, adsorbed with CTPB (Panel I). A specific area of the sample was excited with the electron beam of energy suitable for the constituent elements to emit the X-rays of their characteristic wavelength. The appearance of the K line of fluorine; red—(Panel IV) was observed specifically from the sample alone confirming the adsorption of CTPB. The blue (Panel II) and the green (Panel III) signals from the same region are due to K lines of oxygen and carbon respectively. (c)-(d) Top panel represents the confocal image of HeLa cells, Bottom panel represents intensity profile of the image arising from Hoechst stained nuclei shown as blue peak, Fluorescence intensity of CSP is shown as light green peak, Fluorescence intensity from Alexa 488 fluor antibody is shown as dark green peak. HeLa cells, (3c, I) untreated, stained with Hoechst dye; (3c, II) treated with CSP, where carbon sphere fluorescence always overlap with the nuclear region, showing that the nanosphere localized within the nucleus specifically; (3c, III) untreated, probed with antibody against acetylated histone H3; (3c, IV) treated with HAT activator CTPB (300 μM), probed with antibody against acetylated histone H3. (3d, I) treated with CSP, probed with antibody against acetylated histone H3; (3d, II) treated with HDAC inhibitors TSA (2 μM)/NaBu (1 mM), probed with antibody against acetylated histone H3; (3d, III and IV) treated with CTPB-CSP, probed with antibody against acetylated histone H3.

Figure 4:
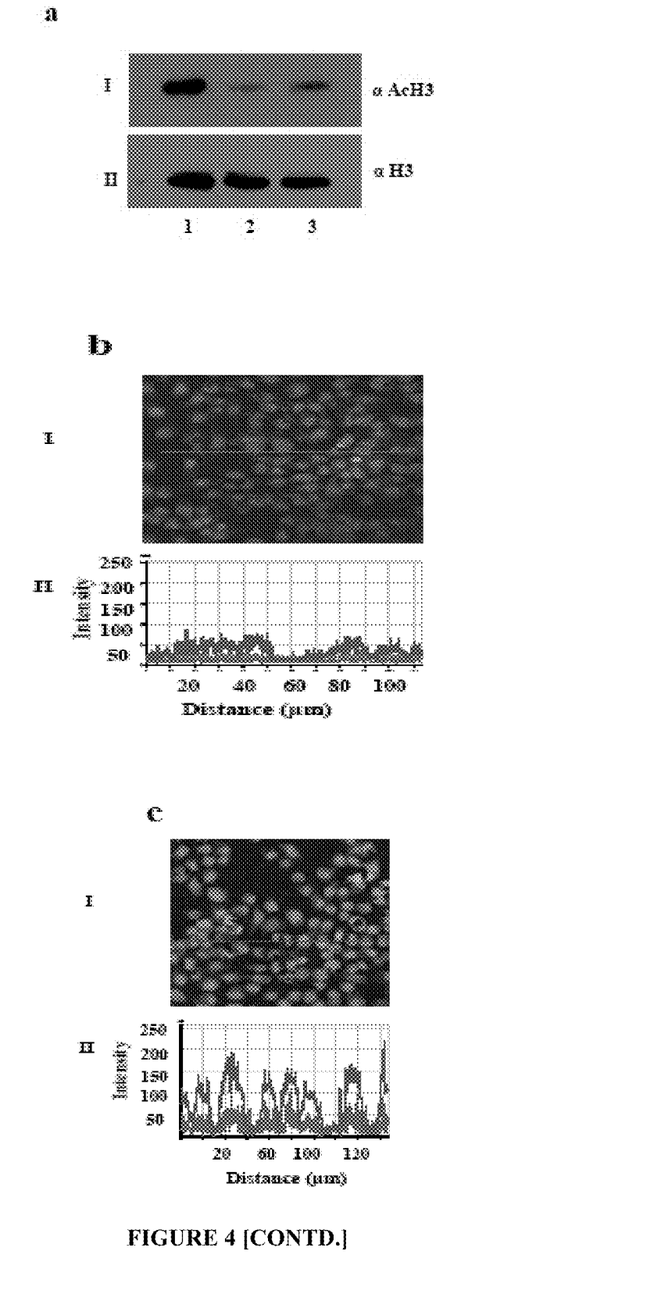

FIG. 4. Hyperacetylation induced by CTPB-CSP activate chromatin, leading to transcriptional activation. (a) Immunoblot analysis of histones isolated from HeLa cells treated with TSA/NaBu (lane 1); CSP (lane 2); CTPB-CSP (lane 3); probed with antibody against acetylated histone H3 (Panel I) and histone H3 (Panel II). Immunofluorescence analysis: (b) of CSP alone, (c) of CTPB-CSP, probed for fluorescent tagged antibody against acetylated p300 HAT. Top panel represents the confocal image of HeLa cells, Bottom panel represents intensity profile of confocal image arising from CSP shown as the light green peak, Fluorescence intensity from alexa 488 fluor antibody is shown as the dark green peak. (d) Immunofluorescence images of HeLa cells treated with CSP, CTPB-CSP, probed for fluorescent tagged antibodies against acetylated histone H3 and RNA polymerase II. Hoechst stained for nuclear visualization and merged images, (e) Intensity profile of the cells treated with CSP and CTPB-CSP. Pink line represents fluorescence intensity from RNA pol II of CSP treated cells. Red line represents fluorescence intensity from RNA pol II of CTPB-CSP treated cells. (f) Expression of a gene (ATF6) upregulated by p300 mediated acetylation investigated by Realtime PCR analysis. Approximately two-fold induction in ATF6 expression on CTPB mediated hyperacetylation (lane 2), as compared to CSP alone treated cells (lane 1) is observed. Error bar indicates the standard deviation of three independent experiments.

Figure 5:
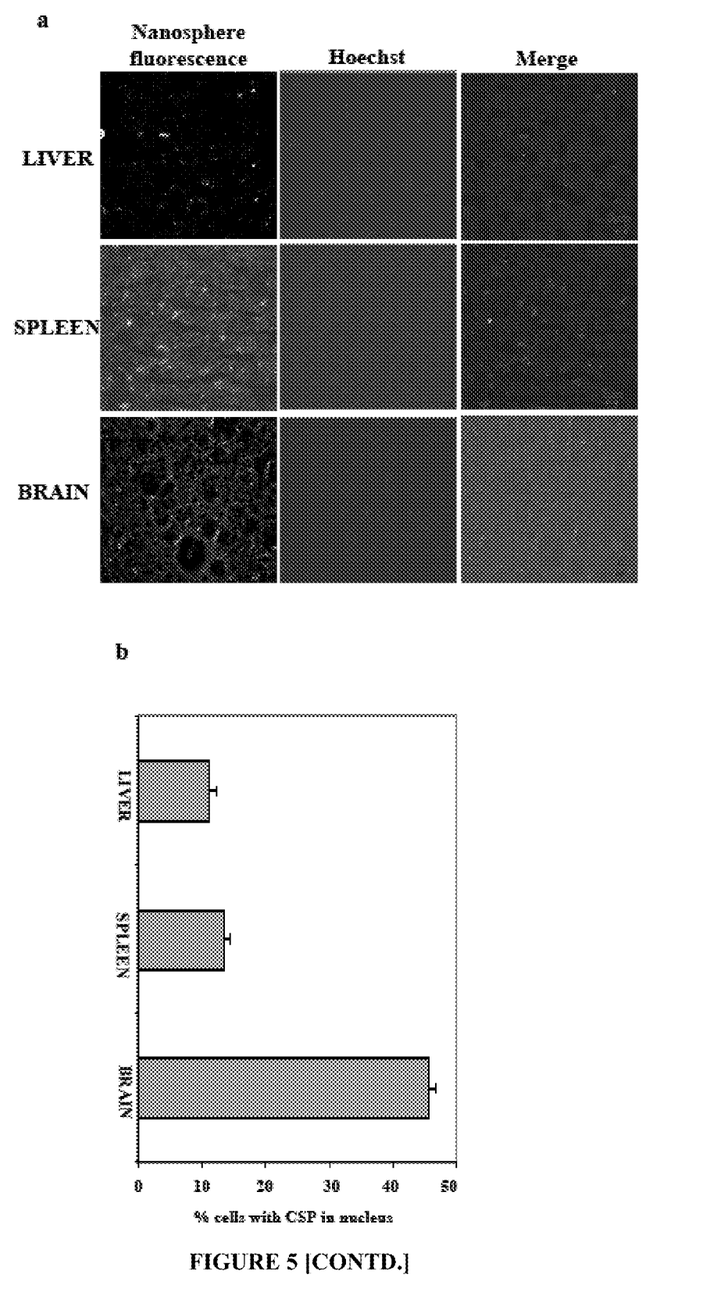
FIG. 5
(a) Confocal images of CSP in animal tissues specifically liver, spleen and brain
(b) Quantification of CSP presence in nucleus of different celltypes
(c) Raman spectra of CSP(I), animal tissue cells without CSP in brain (II), spleen (IV) and liver (IV) and panels III, v and VII are Raman spectra of brain spleen and liver respectively containing the CSP
(d) Immunohistochemical staining CSP alone (Panel I), CTPB-CSP (Panel II)
(e) Graphical representation of CSP presence in different tissues namely Liver, Brain and Kidney after 3, 6 and 9 days

FIG. 5. Carbon spheres, as CTPB carriers are capable of crossing the blood-brain barrier and induce hyperacetylation in vivo. (a) Confocal images of CSP in animal tissues specifically liver, spleen and brain. The CSP fluorescence, Hoechst stained nuclei, merged image of the CSP is represented for each case. (b) Quantification of CSP presence in nucleus of different celltypes. Total number of cells were counted in each tissue and the percentage of those cells with nuclear CSP were determined. Percent of nuclear CSP containing cells in liver, spleen and brain (lane 3). (c) Raman spectra of the CSP (I), animal tissue cells without CSP in brain (II), spleen (IV) and liver (VI). The panels III, V and VII are Raman spectra of brain, spleen and liver respectively, containing the CSP. (d) Immunohistochemical staining using anti acetylated histone H3 antibody of brain tissue from mice treated with CSP alone (Panel I), CTPB-CSP (Panel II) sacrificed after 72 hours. (e) Graphical representation of CSP presence in different tissues of mice monitored for presence of nanospheres for 3, 6 and 9 days of CSP treatment. Shown in blue is percentage of cells with nuclear CSP in liver, red is percentage of cells with nuclear CSP in brain, yellow is percentage of cells with nuclear CSP in kidney. Percentage is calculated by taking into account the cells with nuclear CSP over the total number of cells. Different field of images have been observed and the representation is an average of five such fields with the error plotted as standard deviation.

The technology of the instant application is further elaborated with the help of following examples. However, the examples should not be construed to limit the scope of the invention.

EXAMPLE: 1

The carbon nanospheres are prepared by hydrothermal decomposition of glucose at 180° C. Also, the same can be synthesized in the form of nanotubes by confining the reaction into a porous membrane. The carbon nanospheres thus obtained by hydrothermal decomposition possess a size ranging from 100-500 nm and can be easily dispersed in water and many organic solvents like ethanol, toluene etc. Apart from glucose, other possible precursors which can be used are sucrose, fructose, cyclodextrin, maltose, starch and cellulose. Hence, all these possible precursors can be used to obtain carbon nanospheres of instant invention.

In addition, the carbon nanospheres thus obtained are made up of dense hydrophobic core of polyaromatic units covered by layers of highly functionalized carbon chains of few nm thickness (functionalized with polymeric alcohols, salicylaldehyde groups and $\alpha,\beta$ unsaturated aldehydes) with negatively charged surface. The existence of both hydrophobic core and hydrophilic surface on the carbon spheres helps them to disperse easily in polar and non-polar solvents.

Further, photoluminescence studies on carbon spheres show a weak emission at 560 nm on excitation at 514 nm, attributed to the radiative relaxation of excited electrons (possibly due to the presence of conjugated aromatic systems). This helps to image the carbon spheres in the confocal microscope without the aid of any fluorescent tag over extended periods, which is an added advantage over the risks involved in the case of quantum dots or organic dyes.

Furthermore, the presence of optimum hydrophilicity and hydrophobicity enhances the cell internalization of carbon spheres. The entry of the carbon spheres inside the cells takes about 1 h and at 3 h they reach the perinuclear region followed by their entry into the nucleus. More particularly, these carbon spheres were used to deliver the only known p300 histone acetyltransferase activator CTPB into the cells and thereby induce hyperacetylation and transcriptional activation.

EXAMPLE: 2

FIG. 1a shows the FESEM image of the glucose-derived CSP of size 400 nm in diameter (Supporting Information S2). The CSP were easily dispersible in solvents such as water, ethanol and toluene suggesting the presence of hydrophilic and hydrophobic functional groups on the surface (FIG. 1b). Confocal laser scanning microscopy (CLSM) image of the CSP was obtained by exciting the sample at 514 nm (FIG. 1c). The emission spectrum displayed a broad band centered at 550 nm and a less intense band at 625 nm (FIG. 1d). The 550 nm emission had a stable intensity for about 1 h. The origin of emission at 550 nm is attributed to the surface functional groups[13] like carbonyl and hydroxyl groups, which indeed, disappeared when the functional groups were removed by heat treatment in nitrogen environment (Supporting Information S3).

Method of Preparation of Carbon Nanosphere Adsorbed with CTPB

Carbon nanospheres at a concentration of 2 mg/mL were kept for adsorption onto CTPB (6 mM stock, 3 mg/mL) overnight in a methanol solution after which they were centrifuged at 10000 rpm for 10 min and washed twice with methanol. The sample was dried in air at 30° C. for 6 h. The CTPB adsorbed nanospheres were resuspended in 1 mL water and sonicated for 15 min. The fine suspension was used for all the experimental purposes. Similarly, carbon nanospheres adsorbed with DNA, polycations, peptides, antibodies, RNA and small molecules have been achieved. For experimental purpose, 2-3 month old swiss albino mice were used. Injections were given intraperitoneally. Injection volume was kept constant at 250 μL.

Adsorption of negatively charged molecule like DNA was studied on the surface of the carbon spheres. The adsorption of DNA was carried out by soaking 250 μg dispersed in 10 ml of deionised water containing 5 mg of DNA, pH 7.3 showing signs of adsorption of DNA on carbon spheres. But, increased number of washing in water restores the zeta potential back to −24 mV suggesting weak adsorption. [FIG. 2 (g)].

The carbon sphere has been tested for the adsorption and binding characteristics with polycations and DNA. The following observation with the cations and DNA suggests the possibility of the carbon nanospheres of instant invention acting as a general carrier for nucleic acids and several small molecules by simple adsorption. The consequent nuclear targeting has been performed as performed for CSP-CTPB.

EXAMPLE: 3

The time dependent entry of CSP inside the cell was monitored using CLSM and the results are shown in FIG. 2a (panel I-IV). Entry of CSP inside the nucleus occurred within 3 h, and the extent of nuclear localization was found to increase with time. One of the major concerns regarding the cellular compatibility of carbon based nanoparticles is the toxicity. Therefore, any possible cytotoxicity of the CSP was tested by the MTS (Sodium salt of (3-(4,5-Dimethylthiazol-2-yl)-2,5-diphenyltetrazolium bromide)) based assay system. The viable cells are capable of reducing the MTS salt to a water soluble formazan by the action of mitochondrial reductases.[14] The yellow product obtained on reduction of MTS to formazan is estimated as a measure of cell viability. The presence of CSP within the nucleus did not cause any cytotoxicity even after 24 h of treatment as evident from the absorbance values which were constant throughout the experiment (FIG. 2b, compare lane I with lanes II-VI). On the other hand, the known apoptosis inducing compound, plumbagin[15] lead to a drastic decrease in the absorbance values.

The cellular entry of nanomaterials depends on the optimal concentration of hydrophilic groups[16] on their surface. Besides, the surface charge of the nanoparticles also plays a pivotal role in negotiating with the cell membrane during the entry. As the cell membrane is negatively charged, only those nanoparticles that acquire partly neutral or positive charge at the membrane site can overcome the serum inhibition and expedite their entry.[17] Since the pH of the cellular compartments vary, the surface charge of the CSP at different pH was studied. The zeta potential of the CSP showed a charge reversal with increasing acidity. It varied from a value of −24 mV at pH 7.3 to −4 mV at pH 4 (FIG. 2c). At pH 4, the surface potential had a good overlap in the positive region (FIG. 2d), probably due to the differences in dissociation constant of various carboxylic acid groups present on the surface. When the zeta potential was measured in the cell medium containing serum and other inorganic salts at pH 7.3, a rapid adsorption of inorganic cations ($Na^+$) occurred on the negatively charged CSP decreasing its potential to −17 mV within 30 min (FIG. 2e). Both these factors which modulate the surface charge of CSP facilitate its entry into the cells.

In the cell nucleus, CSP come in close proximity to the highly compact and dynamic nucleoprotein structure, chromatin, composed of DNA, RNA and different proteins (histones and nonhistones). Reversible acetylation of chromatin proteins, predominantly histones by Histone acetyltransferases (HATs) and Histone Deacetylases (HDACs) play a significant role in the dynamicity of chromatin thus regulate transcription, replication and repair.[18] During normal conditions, the enzymatic activity of HATs and HDACs regulate chromatin and transcription factor acetylation in a controlled fashion whereas their imbalance leads to diseases such as cancer, diabetes, cardiovascular diseases and asthma.[19] The well-known new generation drug candidates are the HDAC inhibitors[20] (HDACi). These drugs indirectly induce hyperacetylation which is predominantly nonspecific in nature. Direct activation of a specific HAT is therefore a promising alternative.[21] The only known small molecule HAT activator which could be useful in this context is CTPB[2]. However, its impermeability to the human cells limits its use for molecular probing and therapeutic purposes. Thus, a carrier capable of localizing CTPB directly into the nucleus could circumvent the limitations of HDACi leading to a high therapeutic efficacy.

EXAMPLE: 4

Figure 3:
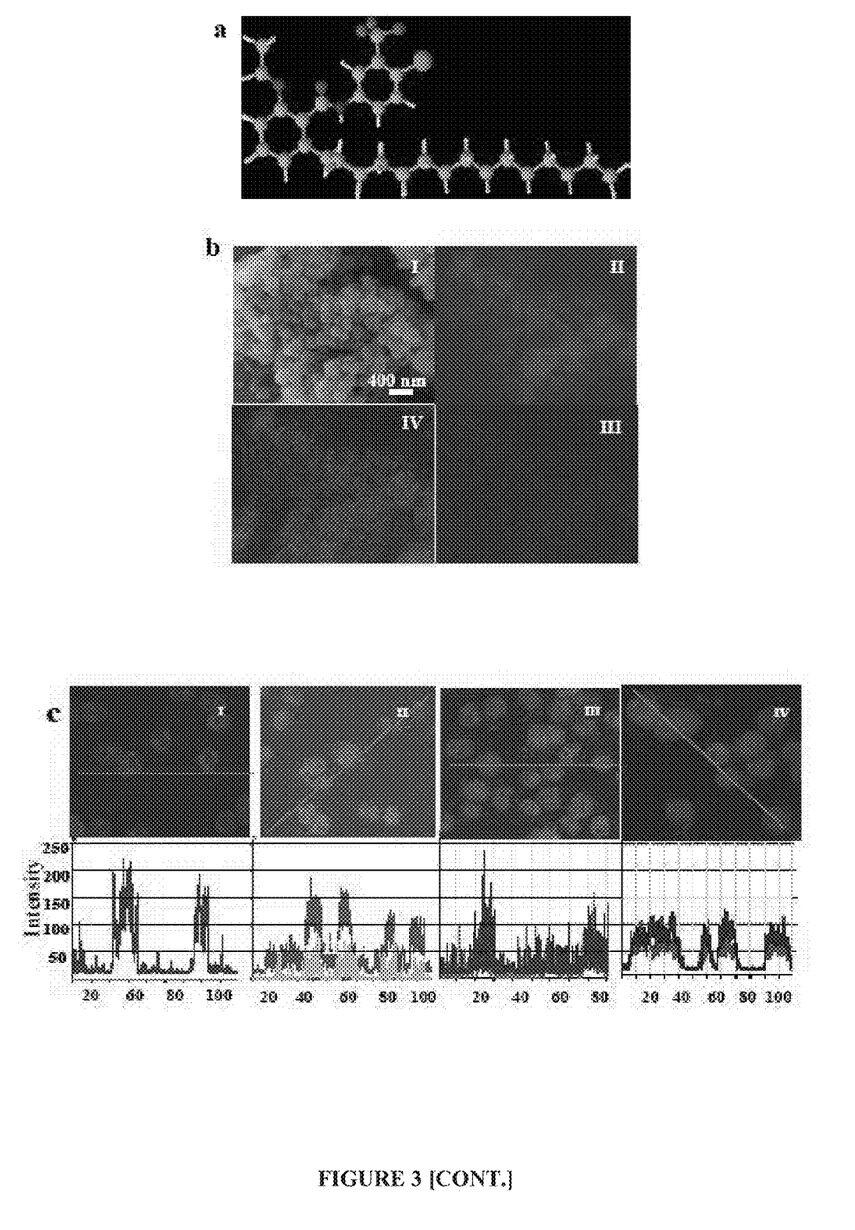

The nuclear targeted entry of CSP was effectively used to carry CTPB (FIG. 3a) inside the mammalian cell nuclei. CTPB was physically adsorbed on the surface of CSP. Energy Dispersive X-ray mapping of the CSP adsorbed with CTPB (FIG. 3b) shows the uniform distribution of the fluorine signal (red region, Panel IV) suggesting the efficient adsorption of CTPB on the surface (For further information, see supporting information, methods). The uptake of CSP and the CTPB adsorbed CSP (CTPB-CSP) by the mammalian cells was monitored by immunofluorescence analysis using acetylated H3 antibody. The intensity of Hoechst stained HeLa cells and the fluorescence from CSP (FIG. 3c I, 3c II) were used as controls. Since CTPB, as such is impermeable to the cell membrane, the hyperacetylation observed in the absence or presence of CTPB alone, did not show any difference (FIG. 3c III, 3c IV). As expected, CSP alone could not alter the acetylation level even after their entry into the nucleus (FIG. 3d, I). On the other hand, addition of CTPB-CSP showed a remarkable 3-4 fold increase in the localized fluorescence intensity of the acetylated H3 antibody (FIG. 3d III, 3d IV) which is comparable to the level of activity (hyperacetylation) of HDACi like trichostatin A (TSA) and sodium butyrate (NaBu) (FIG. 3d II).

EXAMPLE: 5

Immunoblot analysis further confirmed that the CTPB-CSP could induce hyperacetylation of 2.5 fold over the CSP treated cells (FIG. 4a, Panel I, lane 2 and 3). As expected a dramatic hyperacetylation was observed on treating with the HDACi, trichostatin A and Sodium butyrate (lane 1). We have also found that CTPB-CSP induces autoacetylation of p300 in the HeLa cells (FIGS. 4b, 4c) as probed with specific antibody for acetylated p300 (Supporting Information S4). Autoacetylation of p300 enhances its HAT activity[22]. Thus, induction of autoacetylation by CTPB could be the possible molecular mechanism to increase the histone acetylation. The hyperacetylation of chromatin proteins (predominantly histones), induces the transcriptional activity which could be monitored by the recruitment of transcription machineries such as RNA polymerase II.[23] Significantly, we found that CTPB-CSP could not only induce hyperacetylation in its proximal chromatin domain but also increase the recruitment of RNA polymerase II, as evidenced by immunofluorescence images using antibodies against RNA polymerase II (FIG. 4d). The CTPB-CSP treated cells show an approximately three-fold increase in fluorescence intensity as compared to the CSP treated cells (FIG. 4e, pink line vs red line). To further validate the hyperacetylation followed by RNA polymerase II recruitment, the expression of a gene (ATF6), known to be upregulated by p300 mediated acetylation[24] was investigated by Real Time PCR analysis. As expected, hyperacetylation indeed, induce the expression of ATF6 (2 fold) in a physiologically significant manner (FIG. 4f). These data establish the functional significance of the CTPB-CSP induced hyperacetylation.

EXAMPLE: 6

The permeability of CSP was also investigated in mouse model. Mice were injected with nanospheres and were sacrificed after 72 h. The localization of nanospheres in the animal tissues was detected by imaging the fluorescence of the nanospheres (FIG. 5a). The presence of carbon spheres in the brain was found to be highest followed by spleen and liver (FIG. 5b) which was also confirmed by Raman spectrum of a single cell of the fixed animal tissue. Raman Spectrum of CSP has two broad bands at 1340 and 1550 $cm^{-1}$ (FIG. 5c I) which are assigned to the disordered and graphitic structures respectively.[1,25] The Raman spectra of the tissues without CSP are given in FIG. 5c (II, IV and VI). These spectra exhibited a broad band centering around 1440 $cm^{-1}$ and a sharp band at 1650 $cm^{-1}$ arising from the intracellular proteins. The localization of CSP within the cell is confirmed by the presence of bands corresponding to the CSP as shown in FIG. 5c (III, V and VII). A remarkable observation in this context is the ability of 400 nm CSP to cross the blood brain barrier (BBB). There are very few examples of such a large sized particle crossing the BBB. It is well known that the penetration of substances into the brain is limited by the BBB which is formed by the endothelium of brain vessels, the basal membrane and neuroglial cells. Because of this, most drugs do not pass the BBB. It is widely accepted that compounds which are unionized at physiological pH and of low molecular mass can cross the BBB by diffusion mechanisms and other compounds such as amino acids, and hexoses pass into the brain through the specific carriers. A lot of efforts are being put by researchers to make nanoparticles cross the BBB. It has been shown that nanoparticles as large as 300-350 nm have been shown to cross the BBB when coated with glucose derivatives like dextran or polysorbate[26,27,28] In agreement with this, since the CSP are also glucose-derived, the mechanism involved might be similar. The glucose derived CSP could form a complex with certain RNA-protein machineries within the cells facilitating its BBB entry. A detailed study is however essential to conclude the mechanism of uptake across BBB.

EXAMPLE: 7

Furthermore, there was an effective uptake of CTPB-CSP in mice. Tissue sections of the brain of mice sacrificed after 72 h of treatment with CTPB-CSP was subjected to immunohistochemistry with antibody against acetylated histone H3. The immunostained tissue section appears brown due to precipitation of DAB (3',3'-diaminobenzidine tetrahydrochloride). The tissue from CTPB-CSP treated mice showed an increase in acetylation as compared to the tissue from the CSP treated mice (FIG. 5d, Panel II vs panel I). This clearly indicates that CTPB introduced into the animals via CSP could induce hyperacetylation in vivo. As in the cellular system, the CSP in animals do not induce any toxicity as the mice were monitored for about 10 days after injection. The mice were healthy even at the time of sacrifice. The metabolically active organ, liver showed absolutely no CSP after 6 days. The brain tissue retained a minimal amount of carbon nanospheres after 9 days whereas kidney tissue showed the presence of CSP for 6 days only (FIG. 5e). These observations clearly indicate that the CSP are nontoxic to the animals and are being actively turned over in the system.

Although the HDAC inhibitors are involved in HAT activation albeit an indirect manner, they are generally nonspecific and therefore could be relatively toxic in nature. This is due to the functional redundancy that exists among the HDACs thereby making it difficult to have specific HDACi. Recently, it has been shown that HDACi impairs male meiosis in mice thus resulting in reproductive defects.[29] There are several cases like neurodegenerative diseases, cardiovascular diseases, diabetes and cancer, where specific HATs (eg. p300/CBP) are involved in the process of disease manifestation. Therefore, drug molecules targeting specific HAT should be advantageous. In conclusion, the CSP described here are unique molecular transporters owing to their intrinsic fluorescence, surface functionalisation, non-toxicity and green synthetic method. The affinity of carbon spheres for positively charged molecules like polycations (Supporting Information S5) and negatively charged molecules (e.g. DNA; Supporting Information S6) widen the scope of their use. Its immense potential in nuclear-targeted entry has been harnessed by trafficking the cell impermeable HAT activator CTPB, which in turn could induce hyperacetylation in vivo leading to transcriptional activation, giving a positive impetus to the field of therapeutics involving direct HAT activation.

Supporting Information Available: S1—Methods, S2 to S6. This material is available free of charge via the Internet at http://pubs.acs.org.

REFERENCES (1) Sun, X.; Li, Y. Angew. Chem. Int. Ed. 2004, 43, 597.
(2) Balasubramanyam, K.; Swaminathan, V.; Ranganathan, A.; Kundu, T. K. J. Biol. Chem. 2003, 278, 19134.
(3) Michalet, X.; et al. Science 2005, 307, 538.
(4) Barbé, C.; et al. Adv. Mater. 2004, 16, 1959.
(5) Choy, J. H.; Kwak, S. Y.; Jeong, Y. J.; Park, J. S. Angew. Chem. Int. Ed. 2000, 39, 4042.
(6) Nasongkla, N.; et al. Nano. Lett. 2006, 6, 2427.
(7) Zhu, H.; McShane, J. M. J. Am. Chem. Soc. 2005, 127, 13448.
(8) Kam, N. W. S.; Jessop, T. C.; Wender, P. A.; Dai, H. J. Am. Chem. Soc, 2004, 126, 6850.
(9) Liu, Z.; et al. Nat. Nanotech. 2007, 2, 47.
(10) Lacerda, L.; Bianco, A.; Prato, M.; Kostarelos, K. J. Mater. Chem. 2008, 18, 17.
(11) Lacerda, L.; et al. Adv. Mater. 2007, 18, 1480.
(12) Eric, P.; et al. Nat. Mater. 2007, 6, 52.
(13) Liu, H.; Ye, T.; Mao, C. Angew. Chem. Int. Ed. 2007, 46, 6473.
(14) Worle-Knirsch, J. M.; Pulskamp, K.; Krug, H. F.; Nano. Lett. 2006, 6, 1261.
(15) Srinivas, P.; Gopinath, G.; Banerji, A.; Dinakar, A.; Srinivas, G. Mol. Carcinog. 2004, 40, 201.
(16) Liu, Z.; Winters, M.; Holodniy, M.; Dai, H. Angew. Chem. Int. Ed. 2007, 46, 2023.
(17) Xu, P.; et al. Angew. Chem. Int. Ed., 2007, 46, 1.
(18) Berger, S. L. Nature 2007, 447, 407. Review
(19) Swaminathan, V.; Reddy, B. A.; Selvi, B. R; Sukanya, M. S.; Kundu, T. K. Chromatin and Disease, Springer press. 2007, 41, 397.
(20) Mai A. Expert Opin Ther Targets 2007, 11, 835. Review.
(21) Roth, S. Y.; Denu, J. M.; Allis, C. D. Annu Rev. Biochem. 2001, 70, 81. Review.
(22) Thompson, et al., Nat Struct Mol Biol. 2004, 11, 308.
(23) Li, B.; Carey, M.; Workman, J. L. Cell. 2007, 128, 707. Review
(24) Mantelingu, K.; et al. Chem Biol. 2007, 14, 645.

(25) Dinesh, J.; Eswaramoorthy, M.; Rao, C. N. R. *J. Phys. Chem. C,* 2007, 111, 510.
(26) Schroder, U.; Sabel, B. A. *Brain Res.* 1996, 710, 121.
(27) Schroeder, U.; Sommerfeld, P.; Sabel, B. A. *Peptides,* 1998, 19, 777.
(28) Schroeder, U.; Sommerfeld, P.; Ulrich, S.; Sabel, B. A, *J. Pharmacol. Sci.* 1998, 87, 1305.
(29) Fenic, I.; et al. *J. Androl.* 2008, 29, 172.
(30) Michalet, X.; et al. *Science* 2005, 307, 538.
(31) Barbé, C.; et al. *Adv. Mater.* 2004, 16, 1959.
(32) Choy, J. H.; Kwak, S. Y.; Jeong, Y. J.; Park, J. S. *Angew. Chem. Int. Ed.* 2000, 39, 4042.
(33) Nasongkla, N.; et al. *Nano. Lett.* 2006, 6, 2427.
(34) Zhu, H.; McShane, J. M. *J. Am. Chem. Soc.* 2005, 127; 13448.
(35) Kam, N. W. S.; Jessop, T. C.; Wender, P. A.; Dai, H. *J. Am. Chem. Soc,* 2004, 126, 6850.
(36) Liu, Z.; et al. *Nat. Nanotech.* 2007, 2, 47.
(37) Lacerda, L.; Bianco, A.; Prato, M.; Kostarelos, K. *J. Mater. Chem.* 2008, 18, 17.
(38) Lacerda, L.; et al. *Adv. Mater.* 2007, 18, 1480.
(39) Eric, P.; et al. *Nat. Mater.* 2007, 6, 52.

We claim:

1. A composition comprising intrinsically fluorescent carbon nanospheres directly adsorbed with N-(4-chloro-3- trifluoromethylphenyl)-2-ethoxy-6-pentadecyl benzamide, wherein said composition is cell permeable.

2. A process for preparation of the composition of claim 1, said process comprising the step of directly adsorbing the N-(4-chloro-3- trifluoromethylphenyl)-2-ethoxy-6-pentadecyl benzamide over the carbon nanospheres to obtain the composition.

3. The process as claimed in claim 2, wherein the adsorption is followed by centrifugation for a time period ranging from about 7 minutes to about 10 minutes followed by washing, drying and sonicating to obtain the carbon nanospheres with the adsorbed N-(4-chloro-3- trifluoromethylphenyl)-2-ethoxy-6-pentadecyl benzamide.

4. The process as claimed in claim 2, wherein said composition comprises intrinsically fluorescent carbon nanospheres at a concentration of about 2 mg/mL adsorbed with N-(4-chloro-3- trifluoromethylphenyl)-2- ethoxy-6-pentadecyl benzamide at a concentration of about 3 mg/mL.

5. A method of delivering N-(4-chloro-3-trifluoromethylphenyl)-2-ethoxy-6-pentadecyl benzamide inside a cell nucleus, said method comprising step of administering a predetermined amount of the composition of claim 1 to a cell or animal.

6. The method as claimed in claim 5, wherein said composition is permeable to a cell with nucleus targeting ability.

7. The method as claimed in claim 5, wherein said composition is nontoxic.

8. The method as claimed in claim 5, wherein said composition crosses blood brain barrier and gets localized in the brain and also in spleen and liver.

9. The method as claimed in claim 8, wherein said composition activates p300 histone acetyltransferase activity followed by transcription in brain cells.

* * * * *